United States Patent
Auguste et al.

(10) Patent No.: US 12,213,862 B2
(45) Date of Patent: Feb. 4, 2025

(54) INTERFACE DRESSING

(71) Applicant: Urgo Recherche Innovation et Developpement, Chenove (FR)

(72) Inventors: Stéphane Auguste, Ruffey les Echirey (FR); Michel Lamoise, Bessey les Citeaux (FR); Anne-Sophie Danerol, Dijon (FR); Erwann Doulin, Pluneret (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 0 days.

(21) Appl. No.: 16/629,129

(22) PCT Filed: Jul. 11, 2018

(86) PCT No.: PCT/FR2018/051745
§ 371 (c)(1),
(2) Date: Jan. 7, 2020

(87) PCT Pub. No.: WO2019/012226
PCT Pub. Date: Jan. 17, 2019

(65) Prior Publication Data
US 2020/0138630 A1    May 7, 2020

(30) Foreign Application Priority Data

Jul. 12, 2017 (FR) ...................................... 1756599

(51) Int. Cl.
*A61F 13/00* (2024.01)
*A61F 13/01* (2024.01)

(52) U.S. Cl.
CPC .. *A61F 13/01017* (2024.01); *A61F 13/01038* (2024.01)

(58) Field of Classification Search
CPC .......... A61F 13/00017; A61F 13/00038; A61F 13/025; A61F 2013/00604;
(Continued)

(56) References Cited

U.S. PATENT DOCUMENTS 4,341,207 A * 7/1982 Steer .................... A61F 13/0213
602/56
5,340,363 A * 8/1994 Fabo .................. A61F 13/51113
424/447
(Continued)

FOREIGN PATENT DOCUMENTS

DE    19729905 A1 * 1/1999 ............. A61L 15/58
EP    2168607 A1    3/2010
(Continued)

OTHER PUBLICATIONS

International Search Report issued in corresponding International Patent Application No. PCT/FR2018/051745 dated Sep. 10, 2018.

*Primary Examiner* — Ophelia A Hawthorne
*Assistant Examiner* — Michael Milo
(74) *Attorney, Agent, or Firm* — Morgan, Lewis & Bockius LLP

(57) ABSTRACT

An interface dressing (1) comprising an elastomeric matrix (5), the elastomeric matrix (5) being provided with a plurality of through-holes (6), each through-hole (6) having a contour (C) around a central axis (A), in which at least some of the plurality of through-holes (6) are arranged so as to form at least one pattern in which each through-hole (6) is adjacent to at least one other through-hole (6), the adjacent through-holes (6) having contours (C), images of which, when moved in translation in a plane perpendicular to the central axes (A) in order to merge images of said central axes (A) by means of said translational movement, do not become superposed.

23 Claims, 6 Drawing Sheets

Figure 1:
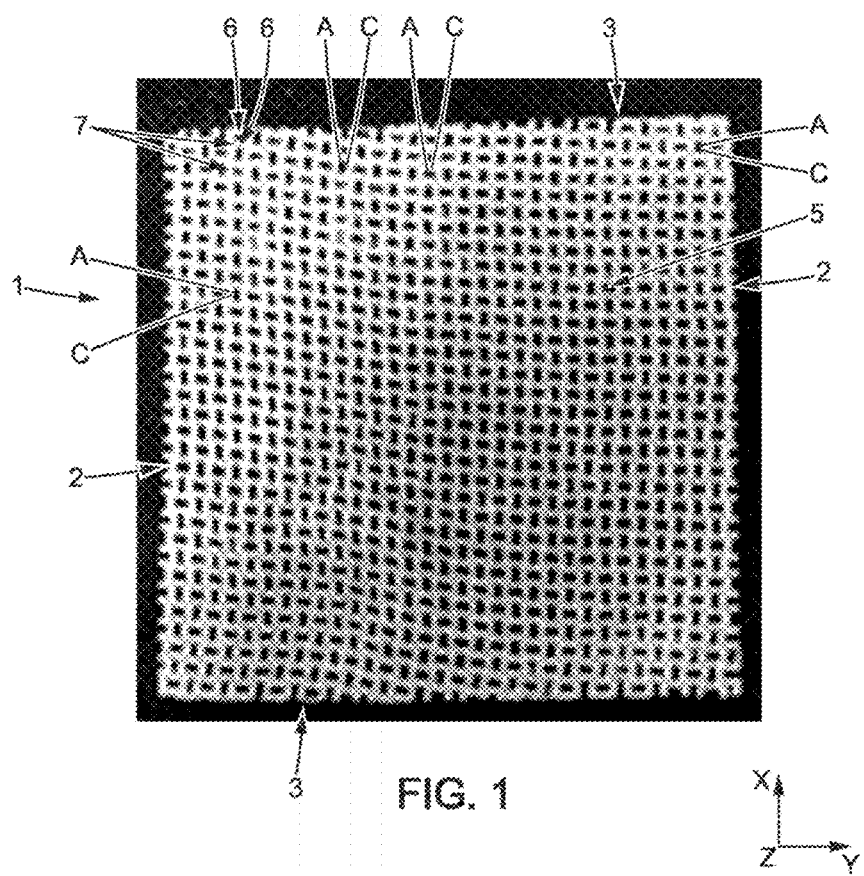

(58) Field of Classification Search
CPC .. A61F 2013/00412; A61F 2013/00902; A61F 2013/00863; A61F 2013/00582; A61F 2013/00685; A61F 2013/00817; A61F 2013/00719; A61F 2013/00089; A61F 2013/00361; A61M 2025/0206; A61M 2025/01213; A61M 2025/0246; A61M 2025/0253; A61M 2025/0266; A61M 25/02; A61B 46/23
USPC .............................. 602/47, 56, 57; 604/180
See application file for complete search history.

(56) References Cited

U.S. PATENT DOCUMENTS

| | | | |
|---|---|---|---|
| 6,270,792 B1* | 8/2001 | Guillemet | A61L 15/34 424/443 |
| 2005/0032952 A1* | 2/2005 | Bonfanti | C09J 167/00 524/492 |
| 2010/0076363 A1* | 3/2010 | Staeger Williams | A61L 26/0052 602/47 |
| 2010/0100022 A1* | 4/2010 | Greener | A61F 13/01038 83/13 |
| 2011/0046526 A1* | 2/2011 | Evans | A61F 13/00017 602/3 |
| 2013/0053748 A1* | 2/2013 | Cotton | A61F 13/01034 602/45 |
| 2014/0081192 A1* | 3/2014 | Wenske | A61L 15/26 602/44 |
| 2015/0012037 A1* | 1/2015 | Goldman | A61B 17/1325 606/216 |
| 2015/0174285 A1* | 6/2015 | Auguste | A61L 15/42 514/532 |
| 2019/0142991 A1* | 5/2019 | Auguste | A61L 15/225 602/46 |

FOREIGN PATENT DOCUMENTS

| | | | |
|---|---|---|---|
| JP | 2008220633 A | * | 9/2008 |
| WO | 87/05206 A1 | | 9/1987 |
| WO | 2014/013175 A1 | | 1/2014 |
| WO | 2015/092315 A1 | | 6/2015 |

* cited by examiner

INTERFACE DRESSING

SUMMARY

The present invention relates to an interface dressing.

More particularly, the present invention relates to an interface dressing comprising an elastomeric matrix provided with a plurality of through-holes.

PRIOR ART

The treatment of wounds with dressings intended to be brought into contact with a wound, providing an interface between the wound and an absorbent compress that is placed on the dressing in order to absorb exudates from the wound, has been known for a long time. Such dressings are usually denoted by the expression "interface dressings".

The interface dressing which has been sold since 2000 by the company Laboratories URGO under the name URGOTUL® is an illustrative example of such interface dressings.

This product, in particular described in example 1 of patent application WO 00/016725, consists of an open-mesh fabric framework, the yarns of which are coated with a cohesive gel so as to leave through-holes which are essentially not blocked and which each have a square contour about a central axis. The gel is formed of a composition consisting of an elastomeric matrix based on triblock copolymers of the ABA (styrene-saturated olefin-styrene) type which is highly plasticized and contains as a dispersion a small amount of hydrophilic particles of a hydrocolloid.

The qualitative and quantitative composition of the elastomeric matrix of this interface dressing gives it notable properties with regard to the promotion of the healing process and, in particular, of fibroblast proliferation.

The URGOTUL® product nevertheless has the drawback, in cases where it is desired to apply it to wounds that are difficult to cover, for example because of their location, of lacking conformability because of the rigidity of its framework.

In order to solve this problem, self-supported interface dressings, that is to say dressings devoid of a framework, have been described in patent application FR 2 936 158. The solutions proposed in this patent application make it possible to obtain products which have good elasticity, and also a rigidity and a cohesion that are sufficient to make it possible to handle them.

Nevertheless, these interface dressings are difficult to use in terms of adapting them to the part of the body on which the wound to be covered is located.

The invention is thus directed toward improving the use of interface dressings, whether they are self-supported or not.

SUMMARY OF THE INVENTION

To this effect, the invention proposes an interface dressing comprising an elastomeric matrix, the elastomeric matrix being provided with a plurality of through-holes, each through-hole having a contour about a central axis, wherein at least one part of the plurality of through-holes is arranged so as to form at least one pattern wherein each through-hole is adjacent to at least one other through-hole, the adjacent through-holes having contours, images of which, when moved translationally in a plane perpendicular to the central axes so as to merge images of said central axes by means of said translational movement, do not become superimposed.

These arrangements make it possible to obtain an interface dressing which can be shaped, and in particular cut or torn, in a controlled manner, in order to adapt it in particular to the dimensions and to the shape of the part of the body on which the wound to be covered is located. The interface dressing that can be shaped in a controlled manner, both at the level of outer edges and at the level of inner openings, offers an improved use.

Furthermore, according to particular arrangements, the interface dressing according to the invention subjected to a tensile force according to a direction parallel to lateral edges keeps its lateral edges straight. This is particularly advantageous during the application of the interface dressing in order to be able to stretch it in one direction, the direction of a length for example, while at the same time retaining one and the same dimension in another perpendicular direction, a width for example.

The elastomeric matrix can consist of an elastomeric composition, the adjacent through-holes of the pattern being separated from one another by a yarn of elastomeric composition.

In particular, the interface dressing may be self-supported. It then consists of solely the elastomeric matrix and is devoid of framework supporting the elastomeric composition.

These arrangements make it possible to obtain an interface dressing which has good elasticity, and good flexibility for adapting to all parts of the body, including those comprising curved surfaces with a small radius of curvature, while at the same time having a certain strength which enables it to stay in place on all parts of the body, including those comprising extended surfaces with a small radius of curvature.

The composition can in particular comprise:
5 to 20% by weight of at least one triblock copolymer of the ABA type, comprising two styrene thermoplastic end blocks A and a central elastomer sequence B which is a saturated olefin, or of a blend of triblock copolymers of the ABA type, comprising two styrene thermoplastic end blocks A and a central elastomer sequence B, which is a saturated olefin, relative to the total weight of the composition, 50 to 80% by weight of at least one plasticizer, 5 to 20% by weight of a resin, the percentages being relative to the total weight of the composition.

The pattern may comprise adjacent through-holes which have identical contours angularly offset from one another about the respective central axes. These arrangements make it possible to obtain a pattern according to which the through-holes are nested in one another.

In particular, the pattern may comprise adjacent through-holes which have contours that are each devoid of rotational symmetry about the central axis.

Additionally or alternatively, the pattern may comprise adjacent through-holes which have contours that each exhibit a rotational symmetry about the central axis with respect to rotation through an angle $2\pi/n$ radians, n being an integer, the contours of the adjacent through-holes of the pattern being angularly offset from one another about the respective central axes with angles different than $2\pi/n$ radians.

The pattern may comprise adjacent through-holes which have rectangular contours.

The rectangular contours of the adjacent through-holes may be arranged orthogonally relative to one another.

The pattern may comprise a network of adjacent through-holes, the central axes of which are aligned in at least a first direction. These arrangements offer shape stability in the first direction.

The central axes of the adjacent through-holes of the network may also be aligned in a second direction perpendicular to the first direction. The interface dressing then also exhibits shape stability in the second direction.

DETAILED DESCRIPTION

Figure 2:
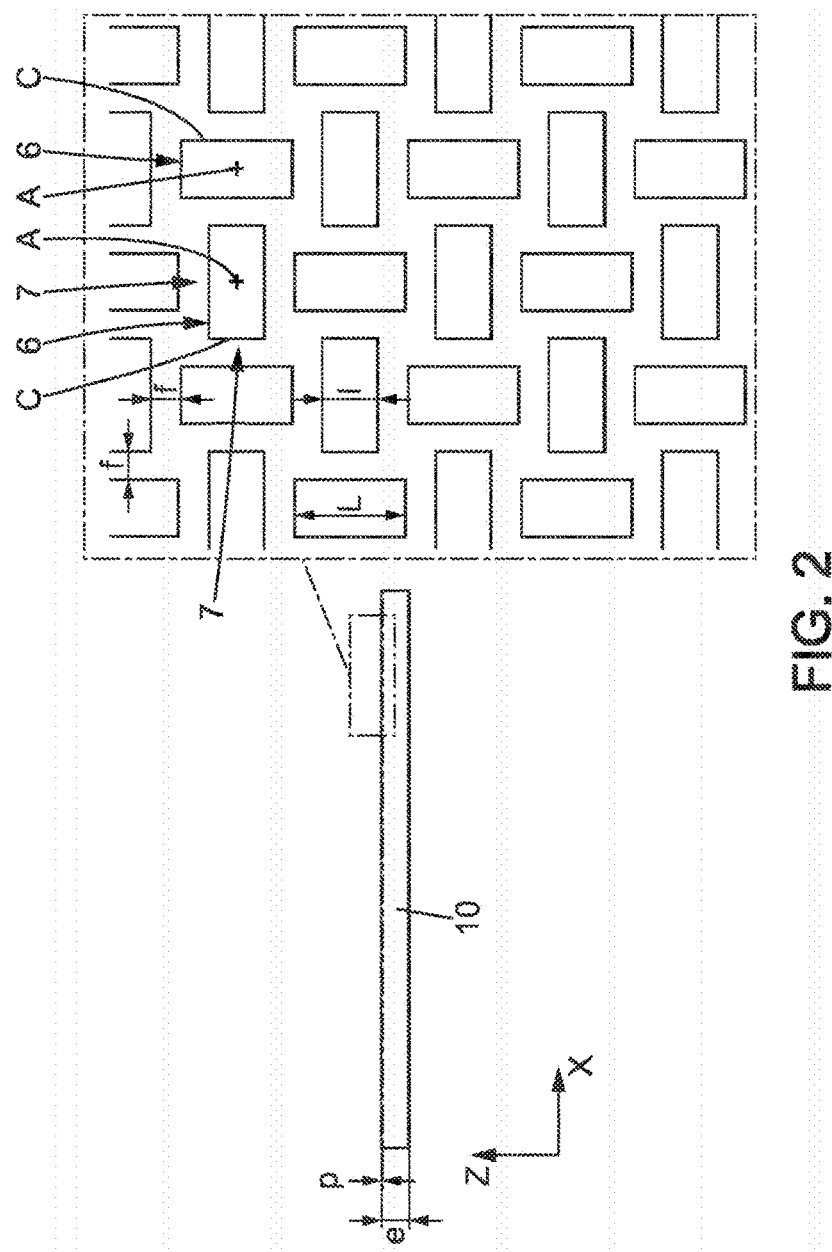
Figure 3:
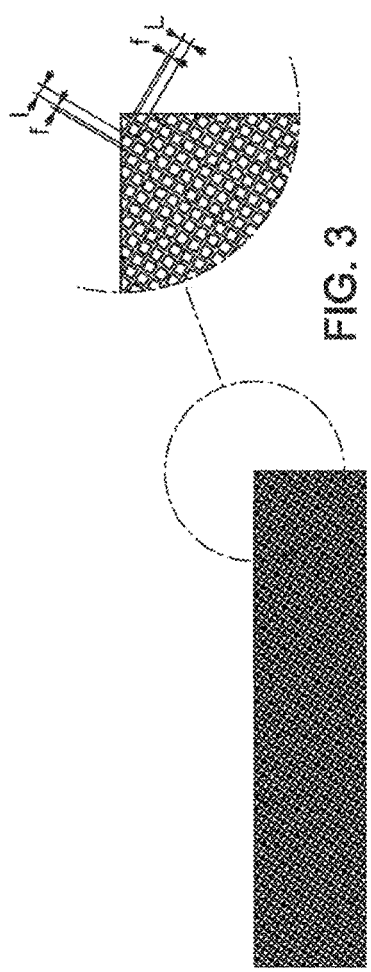
Figure 4:
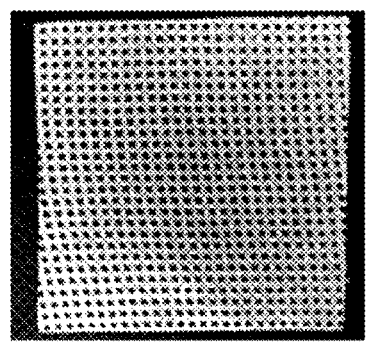
Figure 5:
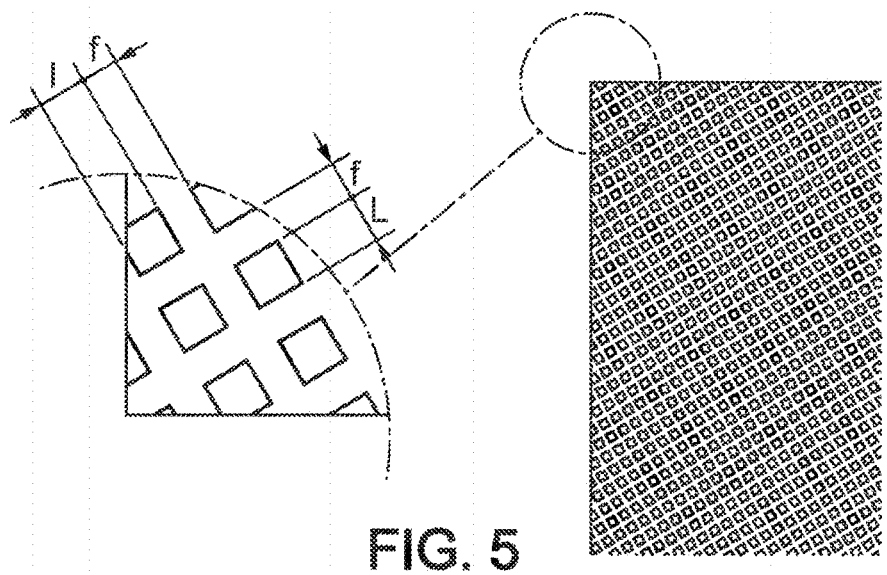
Figure 6:
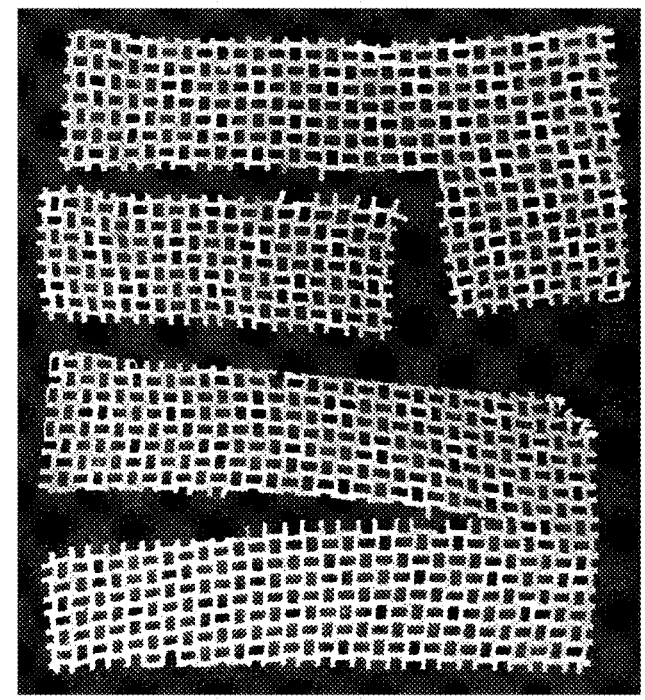
Figure 7:
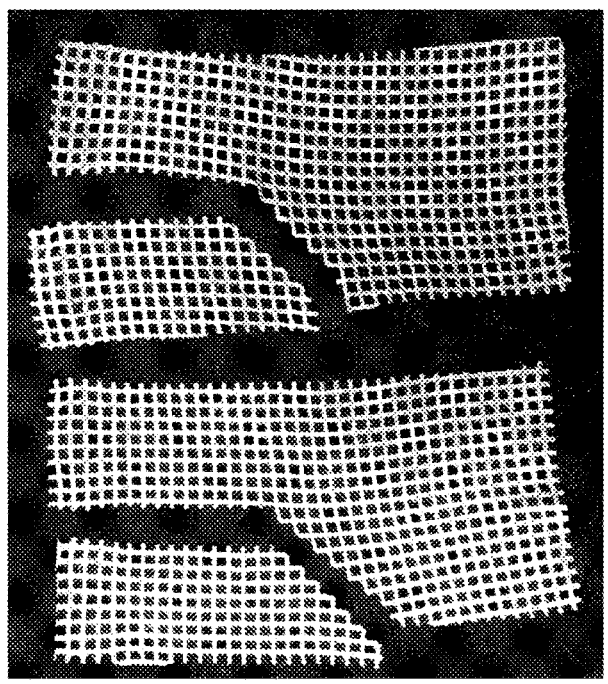
Figure 8:
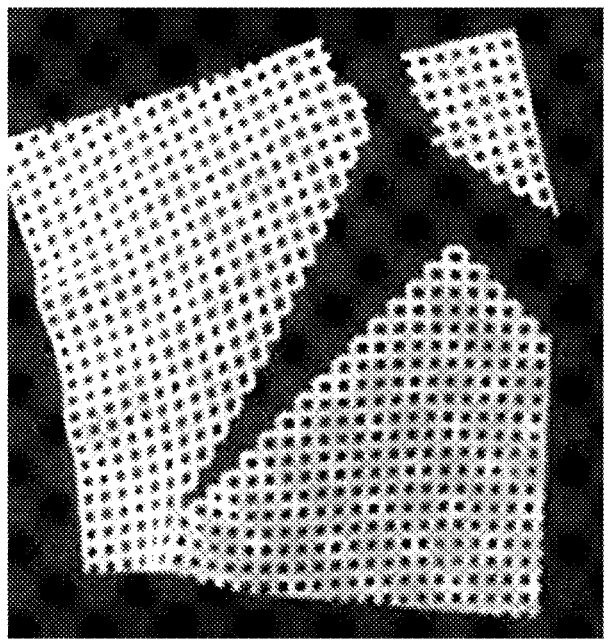
Figure 9:
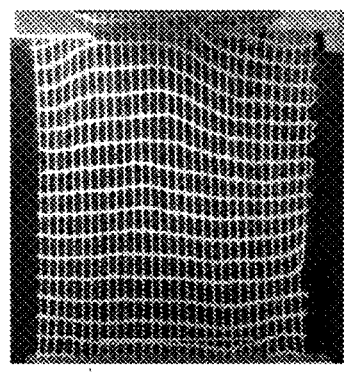
Figure 10:
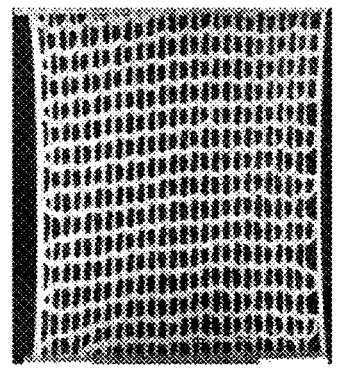
Figure 11:
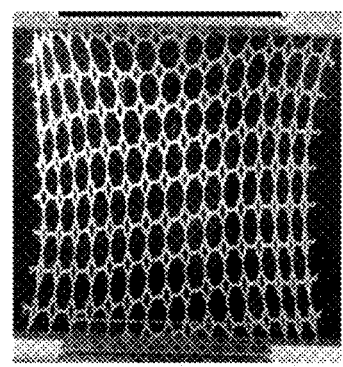
Figure 12:
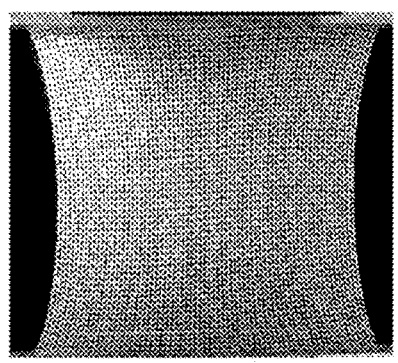

Other subjects and advantages of the invention will emerge on reading the following description of a particular embodiment of the invention, given by way of nonlimiting example, the description being given with reference to the appended drawings wherein:

FIG. 1 represents an interface dressing according to a first example in accordance with an embodiment of the invention, the interface dressing comprising an elastomeric matrix provided with through-holes, the through-holes having identical rectangular contours being arranged such that two adjacent through-holes have contours offset by 90° relative to the respective central axes, FIG. 2 is a representation of a mold for manufacturing the interface dressing according to the embodiment of the invention represented in FIG. 1, the FIG. 3 is a representation of a mold for manufacturing an interface dressing according to a second example in accordance with an embodiment of the prior art, the through-holes having identical square contours, FIG. 4 is a representation of the interface dressing according to the second example in accordance with the prior art, obtained by molding in the mold of FIG. 3, FIG. 5 is a representation of a mold for manufacturing an interface dressing according to a third example in accordance with an embodiment of the prior art, the through-holes having identical square contours of smaller dimensions than those of the second example, FIG. 6 is a representation of the interface dressing according to the first example in accordance with the invention represented in FIG. 1, the interface dressing having been cut, FIG. 7 is a representation of the interface dressing according to the second example in accordance with the prior art represented in FIG. 4, the interface dressing having been cut, FIG. 8 is a representation of the interface dressing according to the third example in accordance with the prior art obtained from the mold represented in FIG. 5, the interface dressing having been cut, FIG. 9 is a representation of the interface dressing according to the first example in accordance with the invention represented in FIG. 1, the interface dressing being stretched in one direction of stretching, FIG. 10 is a representation of an interface dressing according to a fifth example in accordance with an embodiment of the invention, wherein the interface dressing is obtained by three-dimensional (3D) printing, the interface dressing being stretched in the direction of stretching, FIG. 11 is a representation of the interface dressing according to a fourth example wherein the through-holes have identical octahedral contours, the interface dressing being stretched in the direction of stretching, FIG. 12 is a representation of the interface dressing according to a sixth example in accordance with an embodiment of the prior art, the through-holes having identical square contours, the interface dressing being stretched in the direction of stretching.

In the figures, the same references denote identical or analogous elements.

SHAPE OF THE DRESSING

FIG. 1 represents an interface dressing 1 intended to be placed between a wound and an absorbent compress so as to be able to absorb the wound exudates while at the same time making it possible to remove the compress.

The interface dressing 1 comprises an elastomeric matrix 5, which is elastic, supple and flexible while at the same time having a certain strength. Without being limited thereto, the interface dressing 1 is substantially square in shape, having two lateral edges 2 extending in a longitudinal direction X and two transverse edges 3 extending a transverse direction Y, perpendicular to the longitudinal direction X, when it is placed flat on a support surface. The interface dressing 1 has a thickness, measured in a vertical direction Z perpendicular to the longitudinal direction X and transverse direction Y, that is small compared to a length measured in the longitudinal direction X and a width measured in the transverse direction Y.

The elastomeric matrix 5 consists of an elastomeric composition, one particular embodiment of which will be described purely by way of illustration in greater detail in the remainder of the description. In the embodiment represented, the interface dressing 1 is self-supported, that is to say it consists of solely the elastomeric matrix 5 and is devoid of framework supporting the elastomeric composition.

The elastomeric matrix 5 is provided with through-holes 6. The through-holes 6 can be distributed with a density such that a total surface area of the through-holes represents between 20% and 75%, and preferably between 30% and 65%, of a total surface area of the interface dressing 1.

The through-holes 6 are arranged so as to form a pattern in which each through-hole 6 is adjacent to one or more other through-holes 6. In the particular embodiment represented, the pattern comprises through-holes 6 that are regularly distributed so as to form a network of through-holes 6 which are aligned in a first direction, namely the longitudinal direction X, and in a second direction perpendicular to the first direction, namely the transverse direction Y. Each through-hole 6 is then adjacent to two through-holes 6 arranged on either side in the longitudinal direction X and also to two through-holes 6 arranged on either side in the transverse direction Y. The adjacent through-holes 6 are separated pairwise by a yarn 7 of elastomeric composition.

Each through-hole 6 has a contour C about a central axis A. According to the invention, the adjacent through-holes 6 have contours C, images of which, when moved translationally in a plane perpendicular to the central axes A in order to merge images of their central axes A by means of this translational movement, do not become superimposed.

In particular, in FIG. 1, the contours of the adjacent through-holes 6 are identical and rectangular. In order for their images, when moved translationally as mentioned above, not to become superimposed, the contours C of the adjacent through-holes 6 are angularly offset from one another about the respective central axes A. To do this, in the embodiment represented, the rectangular contour C of each through-hole 6 exhibits a rotational symmetry about the central axis A with respect to rotation through an angle of $\pi$ radians, i.e. 180°. The contours of the adjacent through-holes 6 of the pattern are then angularly offset from one another about the respective central axes A with an angle different than π radians and, for example, of π/2 radians, i.e. 90°. Each through-hole 6 extending in either the longitudinal direction X or the transverse direction Y is then adjacent to four through-holes 6 (two in the longitudinal direction X and two in the transverse direction Y) that are arranged orthogonally, that is to say extending in the other of the longitudinal direction X and transverse direction Y. This results in an alternation of through-holes 6 extending longitudinally and of through-holes 6 extending transversely in each of the longitudinal direction X and transverse direction Y. If an imaginary translational movement in a plane perpendicular to the central axes A is applied so as to bring the central axis A of one of the through-holes 6 onto the central axis A of one of the adjacent through-holes 6, the images of the contours thus obtained do not become superimposed.

As represented in FIG. 2, in order to produce the interface dressing 1, the elastomeric matrix 5 is formed into a thin layer by hot casting of the elastomeric composition on a plate 10 etched with the pattern selected for forming through-holes 6, followed by cooling and removal from the mold. The plate 10 has a thickness e, for example of about 10 mm, and the pattern has a depth p adapted to obtain the thickness of the elastomeric matrix 5 that is desired and, for example, is between 0.4 mm and 2 mm, preferably between 0.5 mm and 1 mm, more preferably about 0.8 mm.

Alternatively, the through-holes 6 can be produced by perforation or punching of an elastomeric composition formed beforehand into a thin layer, alone or linked to a temporary support or to a protective film normally used for dressing manufacture.

The through-holes can also be produced by screened coating on a temporary support.

The interface dressing can also be obtained by three-dimensional (3D) printing.

According to a first nonlimiting example given purely by way of illustration, the interface dressing 1 is in the form of a breathable net (or grid) obtained by molding and having:
- a thickness of between 0.4 mm and 2 mm, preferably between 0.5 mm and 1 mm, more preferably of about 0.8 mm,
- a yarn width f between two adjacent through-holes 6 of between 0.3 mm and 4 mm, preferably between 0.5 mm and 2 mm and for example of 0.8 mm,
- a grammage of between 200 g/m$^2$ and 1200 g/m$^2$, preferably of between 300 g/m$^2$ and 800 g/m$^2$, for example of about 390 g/m$^2$,
- a through-hole length L of between 2 mm and 4 mm, for example of about 2.95 mm,
- a through-hole width 1 of between 1 mm and 2 mm, for example of about 1.45 mm.

The through-holes 6 then have a surface area generally of between 0.25 mm$^2$ and 7 mm$^2$.

The invention described in relation to a particular embodiment wherein through-holes 6 of rectangular contour C are regularly distributed is not limited to such a pattern.

The elastomeric matrix 5 could in particular comprise several different patterns.

In other embodiments, the pattern or one of the patterns could comprise adjacent through-holes 6 which have contours C that each exhibit a rotational symmetry about the central axis A with respect to rotation through an angle 2π/n radians, n being an integer. The contours C of the adjacent through-holes 6 of the pattern would then be angularly offset from one another about the respective central axes A with angles different than 2π/n. The pattern or one of the patterns can also comprise adjacent through-holes 6 which have contours C that are each devoid of rotational symmetry about the central axis A.

In addition to the shape of the contour C of the through-holes 6, any other arrangement of through-holes 6 could be envisioned. In particular, the through-holes 6 could be aligned in either of the first and second directions, or distributed otherwise.

Moreover, the interface dressing 1 could comprise a framework supporting the elastomeric composition.

Elastomer

The composition can comprise at least one triblock copolymer of the ABA type.

The block copolymers may be triblock copolymers of the ABA type comprising two styrene thermoplastic end blocks A and a central elastomer sequence B which is a saturated olefin. The saturated olefin sequences B are, for example, ethylene-butylene, ethylene-propylene or ethylene-ethylene-propylene sequences.

In the interests of simplicity, in the present description, the polymeric blocks constituting the abovementioned copolymers are denoted by the nature of their recurring units. Thus, the expression "styrene sequence A" or "block" denotes a poly(styrene) sequence and the expression "saturated olefin sequence" or "block" denotes a poly(saturated olefin) sequence.

According to one embodiment, the composition comprises a blend of two copolymers, said blend comprising at least one copolymer which has a viscosity of between 0.01 and 1 Pa·s measured in a solution at 5% mass/mass in toluene and at least one copolymer having a viscosity of between 0.01 and 0.5 Pa·s measured in a solution at 15% (mass/mass) in toluene.

The triblock copolymers comprising a saturated central sequence are well known to those skilled in the art and are, for example, sold:
- by the company KRATON under the name KRATON® G, and in particular the grades KRATON® G1651, KRATON® G1654, KRATON® G 1657, KRATON® G1652 or KRATON® G1650 and by the company KURARAY under the names SEPTON® and in particular the grades 8006 or 8004 for the poly(styrene-ethylene-butylene-styrene) (abbreviated to SEBS) block copolymers;
- by the company KURARAY under the name SEPTON® for the poly(styrene-ethylene-propylene-styrene) (abbreviated to SEPS) block copolymers and in particular the grades 2005, 2006 or 2063 and for the poly(styrene-ethylene-ethylene-propylene-styrene) (abbreviated to SEEPS) block copolymers and in particular the grades 4033, 4044, 4055, 4077 or 4099.

Among the copolymers which have a viscosity of between 0.01 and 1 Pa·second measured in a solution at 5% (mass/mass) in toluene, mention may be made of the copolymers sold by the company KRATON under the grades KRATON® G 1651 and KRATON® G 1654 and the copolymers sold by the company KURARAY under the grades SEPTON® 2005, 2006, 8006, 4055, 4077, 4044 or 4099.

Among the copolymers which have a viscosity of between 0.01 and 0.5 Pa·second measured in a solution at 15% (mass/mass) in toluene, mention may be made of the copolymers sold by the company KRATON under the grades KRATON® G 1650, KRATON® G 1657 and KRATON® G 1652 and the copolymers sold by the company KURARAY under the grades SEPTON® 2063 or 4033.

These viscosities are measured at 30° C. using a Brookfield viscometer model LVI in a solution in toluene at 5% or 15% mass/mass as a function of the molecular weight of the copolymer.

SEBS, SEPS or SEEPS triblock copolymers having a styrene content of between 25% and 45% by weight relative to the weight of said SEBS, SEPS or SEEPS copolymer will be preferred.

In general, the amount of copolymers in the final composition may be between 5 and 20% by weight, preferably between 7 and 15% by weight, relative to the total weight of the composition.

The use of two SEB block copolymers will be most particularly preferred, and in particular the combination of the KRATON® G 1654 and KRATON® G 1650 copolymers in which the KRATON® G 1654 is present in an amount of from 5 to 10% by weight, relative to the total weight of the composition, and the KRATON® G 1650 is present in an amount of from 2 to 5% by weight, relative to the total weight of the composition.

Preferably, this blend of two copolymers will thus comprise at least 5 to 10% by weight of a copolymer which has a viscosity of between 0.01 and 1 Pa·second measured in a solution at 5% mass/mass in toluene and at least 2 to 5% of a copolymer having a viscosity of between 0.01 and 0.5 Pa·second measured in a solution at 15% (mass/mass) in toluene, relative to the total weight of the composition.

The Resins

The elastomeric matrix may also contain a resin. The resins used are those normally used in this type of matrix.

Among these resins, mention will be made by way of example of the resins generally used by those skilled in the art, such as modified polyterpene or terpene resins, hydrogenated rosin resins, polymerized rosin resins, rosin ester resins, hydrocarbon-based resins, mixtures of aromatic and aliphatic resins, etc. By way of example, mention may be made of a synthetic resin formed of C5/C9 copolymers, sold by the company CRAY VALLEY under the name WING-TACK 86.

Among the resins of hydrogenated hydrocarbon(s), mention will be made of the resins sold for example by the company ARAKAWA under the name ARKON®.

The composition may also comprise at least one tackifying resin in order to give them an adhesive nature facilitating their placement on the wound.

The tackifying resins that can optionally be used in the composition are chosen in particular from low-molecular-weight polyisobutylenes. In general, the use of hydrogenated resins such as the Escorez® resins of the 5000 series, and even more preferentially the Escorez 5380® resin, is preferred.

The resins preferentially used in the composition are aromatic hydrocarbon-based resins, that is to say resins based only on aromatic monomers. They differ from the aliphatic resins, based on aliphatic monomers only, or from the aliphatic/aromatic resins based on aliphatic and aromatic monomers. Without wishing to be bound by any theory, it appears that these resins have good solubility in the block A of the ABA copolymers and reinforce this styrene block, thereby improving the cohesion of the final elastomeric matrix obtained.

In particular, the aromatic monomer is alpha-methylstyrene. Thus, according to one embodiment, the aromatic hydrocarbon-based resin is chosen from resins of alpha-methylstyrene homopolymers and copolymers.

Among the aromatic resins tested, a certain number of them were not entirely satisfactory. Indeed, some resin grades, because of their high softening point, need to be heated to high temperatures (above 140° C.) in order to produce the composition of the invention. By working at such temperatures, there is a risk of evaporation of the plasticizer. When hydrocolloids (such as carboxymethylcellulose) or active agents are added to the composition, there is a risk that they will be degraded.

Thus, the resins used in the compositions are the alpha-methylstyrene-type resins of which the softening point is between 80 and 125° C., preferably between 90 and 110° C.

The softening point is measured according to the ISO 4625 standard ("Ring and Ball" method).

Preferably, the resin is an alpha-methylstyrene resin having a softening point between 95 and 105° C. or between 115 and 125° C., or a poly(styrene-co-alpha-methylstyrene) resin having a softening point between 95° C. and 115° C.

The preferential resins above are well known to those skilled in the art and are commercially available, for example sold under the following trade names:

Sylvares SA 100 and Sylvares SA 120 from Arizona Chemical: alpha-methylstyrene resins having a softening point between 95 and 105° C. or between 115 and 125° C. respectively, the Cleartack W90 or Norsolene W90 resin from Cray Valley: poly(styrene-co-alpha-methylstyrene) resin having a softening point between 85 and 95° C., the Kristalex 3100LV, Kristalex F100, Kristalex 3105SD and Kristalex F115 resins from Eastman: poly(styrene-co-alpha-methylstyrene) resins having a softening point of 100° C., or between 96 and 104° C. or of 105° C., or between 114 and 120° C. respectively.

The resin is preferably present in an amount of from 5% to 20%, preferably 5% to 15% by weight, relative to the total weight of the composition.

In order to produce the interface dressings, the copolymer blend and the resin present in the composition are combined with one (or more) plasticizing compound(s).

The plasticizers that can be used are well known and are intended to improve the stretching, suppleness, extrudability or processing properties of the copolymers. To this effect, use will be made of one or more plasticizers if necessary.

In general, liquid compounds, compatible with the saturated olefin central sequence of the abovementioned block copolymers, will be preferred as plasticizers.

Among the plasticizing compounds that can be used to this effect, mention will in particular be made of plasticizing mineral oils.

Alternatively, it is also possible to use synthetic products based on liquid mixtures of saturated hydrocarbons, such as for example the products sold by the company TOTAL under the name GEMSEAL® and in particular the GEMSEAL® 60 product which is an isoparaffinic mixture derived from a totally hydrogenated petroleum cut.

Use will preferably be made of plasticizing oils and in particular of mineral oils formed of compounds of paraffinic or naphthenic nature, or mixtures thereof, in variable proportions.

Plasticizing mineral oils that are particularly preferred are formed of mixtures of compounds of paraffinic and naphthenic nature, and in particular of such mixtures wherein the proportion of compounds of paraffinic nature is predominant.

Among the plasticizing oils that are particularly suitable, mention may be made of the products sold by the company SHELL under the names ONDINA® and in particular ONDINA® 919 or the oil sold by the company PETRO CANADA under the reference PURETOL® 9D or the BLANDOL oil sold by Sonneborn or else the Pionier 2076P oil sold by Hansen & Rosenthal.

In addition to the oils, the plasticizer may comprise petroleum jelly. The petroleum jelly used in the composition is a petroleum jelly in accordance with the French Pharmacopea that is commercially available.

The petroleum jelly is present in an amount of from 1% to 30%, preferably 5% to 25% by weight, relative to the total weight of the composition.

The plasticizer is present in an amount of from 50% to 80%, preferably 60% to 70% by weight, relative to the total weight of the composition.

Preferably, the plasticizer consists of a mixture of mineral oil and petroleum jelly, the mineral oil being present in an amount ranging from 45% to 60% by weight relative to the total weight of the composition, the petroleum jelly being present in an amount ranging from 5% to 20% by weight relative to the total weight of the composition.

Active Agent

The composition may also comprise at least one active agent which makes it possible to induce or accelerate healing or can have a favorable role in the treatment of a wound.

Among these active substances, mention may be in particular be made, by way of examples, of:
  healing-promoting agents such as retinol, vitamin A, vitamin E, N-acetylhydroxyproline, *Centella asiatica* extracts, papain, silicone, essential oils of thyme, niaouli, rosemary, sage, hyaluronic acid, potassium sucrose octasulfate, sucralfate, allantoin, metformin;
  antibacterial agents such as silver salts or complexes (such as silver sulfates, silver nitrates, silver sulfamides or else silver-based zeolites), zinc salts or copper salts, metronidazole, neomycin, penicillins, clavulanic acid, tetracyclines, minocycline, chlorotetracycline, aminoglycosides, amikacin, gentamicin, probiotics;
  antiseptics such as chlorhexidine, trichlosan, biguanide, hexamidine, thymol, lugol, iodinated povidone, benzalkonium chloride and benzethonium chloride;
  painkillers such as paracetamol, codeine, dextropropoxyphene, tramadol, morphine and its derivatives, corticoids and their derivatives;
  local anesthetics such as lidocaine, benzocaine, dibucaine, pramoxine hydrochloride, bupivacaine, mepivacaine, prilocaine, etidocaine;
  anti-inflammatories such as nonsteroidal anti-inflammatories (NSAIDs), aspirin or acetylsalicylic acid, ibuprofen, ketoprofen, flurbiprofen, diclofenac, aceclofenac, ketorolac, meloxicam, piroxicam, tenoxicam, naproxen, indomethacin, naproxcinod, nimesulid, celecoxib, etoricoxib, parecoxib, rofecoxib, valdecoxib, phenylbutazone, niflumic acid, mefenamic acid.

Of course, the composition may also comprise one or more other compounds known for their action in the detersion phase, such as for example:
  enzymes;
  urea.

Preferably, the healing-promoting agent is chosen from the healing-promoting agents retinol, vitamin A, vitamin E, N-acetylhydroxyproline, *Centella asiatica* extracts, papain, silicone, essential oils of thyme, niaouli, rosemary, sage, hyaluronic acid, potassium sucrose octasulfate, sucralfate, allantoin, metformin, and preferably the healing-promoting agent is metformin.

The composition comprises 0.1% to 15% of active agents, preferably 1% to 10% by weight, relative to the total weight of the composition.

Hydrocolloid

In the context of the production of interface dressings, with support or with framework for wound healing, the composition may comprise hydrophilic particles of a hydrocolloid (or hydrocolloid particles).

These particles in fact allow the painless removal of an interface dressing and the maintaining of a moist environment at the level of the wound in order to promote healing.

To this effect, a small amount of hydrophilic particles of a hydrocolloid is thus either placed at the surface of the elastomeric matrix once said matrix is formed, or preferably homogeneously dispersed within the composition.

The term "hydrocolloid" or "hydrocolloid particles", is intended to denote herein any compound normally used by those skilled in the art for its ability to absorb aqueous liquids such as water, physiological saline or exudates from a wound.

As suitable hydrocolloids, mention may for example be made of pectin, alginates, natural plant gums such as in particular Karaya gum, cellulose derivatives such as carboxymethylcelluloses and their salts of an alkali metal such as sodium or calcium, and also synthetic polymers based on acrylic acid salts, known under the name "superabsorbents", such as for example the products sold by the company CIBA Specialty Chemicals under the name SALCARE® SC91 and also the mixtures of these compounds.

Some of these superabsorbents described as "microcolloids" because they have a particle size of less than 10 micrometers can of course also be used.

The preferred hydrocolloids are alkali metal salts of carboxymethylcellulose, and in particular sodium carboxymethylcellulose (CMC).

The size of the hydrocolloid particles is generally between 50 and 100 microns, advantageously about 80 microns.

In general, the amount of hydrocolloid particles incorporated into the composition will advantageously be less than or equal to 25% by weight, advantageously about from 2% to 20% by weight, preferably from 5% to 18% by weight, more preferably from 10% to 15% by weight, relative to the total weight of said composition.

If the hydrocolloid particles are placed at the surface of the elastomeric matrix once said matrix is formed, the amount thereof will preferably be about from 1% to 10% and more particularly from 2% to 5% by weight, relative to the total weight of said elastomeric matrix.

The choice of an amount of hydrocolloid particles included in these value ranges is important for the production of an interface dressing, and in particular an aerated self-supported interface dressing, in order to prevent the gelling of the composition leading to the closing of the through-holes during exudate absorption.

Antioxidants

The composition may also comprise antioxidants.

The term "antioxidants" is intended to denote herein the compounds commonly used by those skilled in the art to ensure the stability of the compounds that are part of the formulation of the compositions, in particular with respect to oxygen, heat, ozone or ultraviolet radiation.

As examples of suitable antioxidants, mention may in particular be made of phenolic antioxidants such as in particular the products sold by the company BASF under the names IRGANOX® 1010, IRGANOX® 565, IRGANOX® 1076.

In general, these antioxidants may be used alone or in combination in an amount of about from 0.05% to 1% by weight, preferably from 0.05% to 0.2% by weight, relative to the total weight of the composition.

The use of the IRGANOX® 1010 product in an amount of between 0.05% and 0.2% by weight, relative to the total weight of the composition, will be preferred.

Adjuvant

By way of adjuvants that can be used in the composition, mention may be made of compounds known to promote the release of active agents, such as for example the Montanox® 80 or Sepinov® EMT 10 products (copolymer of the salt of 2-methyl-2-[(1-oxo-2-propenyl)amino]-1-propanesulfonic acid and of the 2-hydroxyethyl ester of propenoic acid or of the mixture of 2-octyl-1-dodecanol, of D-xylopyranoside, of 2-octyldodecyl and of polyethylene glycol 30 dipolyhydroxystearate) which are commonly used in the URGOTUL® products which incorporate active agents.

These adjuvants may be used in an amount of about from 0.01% to 10% by weight, preferably 0.05% to 5% by weight, relative to the total weight of the elastomeric matrix.

Of course, the particular embodiments which have just been described can be implemented separately or according to any one of the combinations thereof.

The composition according to the invention makes it possible, in particular, to produce a self-supported interface dressing or an interface dressing having a framework or a support.

In the context of the production of an interface dressing, the use of a composition which comprises compounds (copolymers, mineral oil, petroleum jelly, antioxidant and hydrocolloids) of the same nature as, or identical to, those used in the URGOTUL® product will be preferred.

Elastomeric Matrix

In order to produce an interface dressing, the composition will be formed in a thin layer, with through-holes, preferably arranged in a manner distributed in said layer so as to form an elastomeric matrix.

Dressing

The self-supported interface dressing comprises an elastomeric matrix which is in the form of a thin layer having through-holes so as to allow exudates to pass through, obtained from a composition comprising:
- 5 to 20% of at least one triblock copolymer of the styrene—saturated olefin-styrene type,
- 50 to 80% by weight of at least one plasticizer,
- 5 to 20% of at least one resin,
- the percentages being relative to the total weight of the composition.

According to one preferred embodiment, the self-supported interface dressing comprises an elastomeric matrix which is in the form of a thin layer having through-holes so as to allow exudates to pass through, obtained from a composition comprising:
- 5 to 20% of at least one triblock copolymer of the styrene—saturated olefin-styrene type,
- 50 to 80% by weight of at least one plasticizer,
- 5 to 20% of at least one resin of alpha-methylstyrene type, the softening point of which is between 80 and 125° C., preferably between 90 and 110° C.,
- the percentages being relative to the total weight of the composition.

Preferably, the interface dressing does not adhere to latex gloves. To do this, the composition may, preferably, comprise:
- for 100 parts by weight of a blend P of two specific triblock copolymers of the styrene—saturated olefin—styrene type, a first which has a viscosity of between 0.01 and 1 Pa·s as measured in a solution at 5% (mass/mass) in toluene and a second which has a viscosity of between 0.01 and 0.5 Pa·s as measured in a solution at 15% (mass/mass) in toluene;
- from 300 to 1000 parts by weight of a plasticizer H, preferably a plasticizing oil; and
- from 90 to 600 parts by weight of petroleum jelly V;

it also being specified that:
- the total amount, represented by P+H+V, of elastomer blend, of the plasticizer and of the petroleum jelly is between 490 and 1700 parts by weight;
- the ratio between the total amount of the elastomer blend, the plasticizer and the petroleum jelly and the amount of petroleum jelly, represented by P+H+V/V, is less than 11;

said blend of two copolymers comprises at least 20% by weight of the first copolymer,
the composition also comprising from 5 to 20% by weight of a resin,
the percentages being relative to the total weight of the composition.

In order to protect the composition from the exterior environment, the interface dressing may be covered, preferably on each of its faces, with a temporary protective film that will be removed before use by the user.

In order to further facilitate the handling of the interface dressing, in particular if it is self-supported, these two temporary protective films may be replaced with a single protector as described in patent application WO 2008/145 884 or in patent application WO 2015/018720, the particular structure of which facilitates the application of the dressing to the wound.

Of course, the particular embodiments that have just been described can be implemented separately or according to any one of the combinations thereof.

Preparation of the Self-Supported Interface Dressings

Interface dressings according to first, second, third, fourth, fifth and sixth examples, hereinafter also denoted respectively examples 1, 2, 3, 4, 5, 6, are produced for the purpose of carrying out comparative tests.

The composition of examples 1 to 6 was produced using the following constituents in the proportions, expressed as weight percentage, mentioned in table 1.

Elastomers: poly(styrene-ethylene-butylene-styrene) (abbreviated to SEBS) block copolymers:
- KRATON® G 1654 ES viscosity at 5% (mass/mass) in toluene: 0.02 Pa·s
- KRATON G 1651
- KRATON® G 1650 E viscosity at 15% (mass/mass) in toluene: 0.2 Pa·s Plasticizer: Pionier 2076P mineral oil sold by Hansen & Rosenthal
- petroleum jelly: Vaseline Codex® A sold by the company AIGLON Antioxidant: IRGANOX® 1010 sold by the company BASF
- hydrocolloid: sodium carboxymethylcellulose CMC BLANOSE® 7H4XF sold by the company ASHLAND, Resin:
- Sylvares SA 100, alpha-methylstyrene resin having a softening point between 95 and 105° C., sold by Arizona Chemical Manufacture of the Composition The plasticizer, the hydrocolloid and the petroleum jelly were successively introduced, at a setpoint temperature of 90° C., into a vertical mixer and the mixture was stirred until a homogeneous mixture was obtained.

The copolymer(s) and the antioxidant were then introduced, the setpoint temperature was increased to 150° C., then the resulting mixture was stirred until a homogeneous mixture was obtained. The resin(s) where appropriate were then added.

The resulting mixture was then left to cool, then the mixer was emptied.

In a second step, the mixture is reheated to 125° C. then deposited on an etched plate, itself heated to 120° C. The mixture thus deposited is levelled off with a scraper (also heated to 120° C.) so that it is distributed into the mold cavity.

The etched plate is then cooled to a temperature of 40 to 50° C. The cooled mixture is then manually removed from the etched plate.

For example 5, the mixture is reheated to 120° C. via a heating vessel. The material is then transported, by means of pipes heated to 90° C., to heating heads equipped with 0.5 mm nozzles maintained at 98° C., the orifice diameter of which is variable as required. The assembly of pipes, heads and nozzles is installed on a gantry XYZ, which allows the material to be deposited in the three dimensions. The self-supported interface dressing is produced in two steps: first, the exterior contour, then the drawing of the interior of the dressing (the path represents steps offset by a previously defined increment).

For example 6, the mixture is reheated to 130° C. and coated onto a heat-set knit with weft yarns, made of polyester yarns, manufactured by the company MDB TEXINOV under the reference 601.

In FIGS. 3 to 5, the interface dressings according to the second and third examples are in accordance with embodiments of the prior art. In these interface dressings according to the second and third examples, the through-holes are aligned and the contours thereof are identical squares with one and the same orientation. These interface dressings differ from one other by virtue of their dimensions, namely their length L and their width 1.

The fourth example of an interface dressing that can be seen in FIG. 11 comprises through-holes which are aligned and the contours of which are in the shape of identical octahedra with one and the same orientation.

The fifth example of an interface dressing that can be seen in FIG. 10 is in accordance with an embodiment of the invention and differs from the first example in that it is obtained by three-dimensional (3D) printing.

The sixth example of an interface dressing is in accordance with an embodiment of the prior art like the second and third examples, from which it differs by virtue of the dimensions.

The main characteristics of the interface dressings according to the second, third, fourth, fifth and sixth examples are given in tables 1, 2 and 3 below.

TABLE 1

|  | Mass of ex. 1, 2 and 3 | Mass of ex. 4 and 5 | Mass of ex. 6 |
|---|---|---|---|
| No of internal mass | 4488 | 3973 | ~~1305~~ |
| Kraton G1654 ES | 7.8 | 5.7 |  |
| Kraton G 1650 E | 3.5 | 2.6 |  |
| Kraton G 1651 |  |  | 4.931 |
| Pionier 2076P | 53.5 | 61.5 | 74.947 |
| Vaseline Codex A | 12 | 15 | 5.000 |
| CMC Blanose 7H4XF | 13 | 15 | 14.999 |
| Irganox 1010 | 0.2 | 0.2 | 0.123 |
| Sylvares SA 100 | 10 |  |  |

TABLE 2

|  | Pattern | Through-hole of dimensions L × 1 (mm) | Yarn width f (mm) | Depth p or thickness (μm) | Surface area coated (%) |
|---|---|---|---|---|---|
| Ex. 1 | Tetris rectangles | 2.95 × 1.45 | 0.8 | 800 | 52.5 |
| Ex. 2 | Squares | 2 × 2 | 0.8 | 800 | ≈50 |
| Ex. 3 | Squares | 2 × 2 | 1.6 | 750 | 69 |
| Ex. 4 | "Cabochon" | 1.95 × 1.95 | 0.8 | 500 | 53 |
| Ex. 5 | Rectangle | 3.0 × 2.0 | 1.3 | 1100 | 42 |
| Ex. 6 | Square | 0.8 × 0.8 | 0.4 | 260 | 40 |

TABLE 3

|  | Pattern | Mock-up thickness (μm) | Mock-up grammage (g/m²) |
|---|---|---|---|
| Ex. 1 | Tetris rectangles | 755 ± 60 | 390 ± 12 |
| Ex. 2 | Squares | 815 ± 35 | 330 ± 2 |
| Ex. 3 | Squares | 700 ± 35 | 400 ± 13 |
| Ex. 4 | "Cabochon" | 350 | 129 |
| Ex. 5 | Rectangle | 1100 | 563 |
| Ex. 6 | Squares | 260 | 158 |

In FIGS. 6 to 8, the interface dressings according to the first, second and third examples are manually cut. It is noted that the interface dressing of the first example produced in accordance with the invention cuts linearly from an initiator, which is not the case with the interface dressings according to the second and third examples in accordance with embodiments of the prior art.

In FIGS. 9 to 12, by means of a tensile testing machine at constant elongation speed, the interface dressings according to the first example (FIG. 9), fifth example (FIG. 10), fourth example (FIG. 11) and sixth example (FIG. 12), having a width 1 of 10 cm, are subjected to a tensile force in a direction of stretching parallel to their length, at a speed of 100 mm/min, with a distance between the jaws of 5 cm, up to an elongation of approximately 70% of their elongations at break. The interface dressings are held at this elongation for a few seconds in order to observe the geometry of their lateral edges.

When they are subjected to a tensile force, the interface dressings of the first and fifth examples (FIGS. 9 and 10), in accordance with the invention, whether they are obtained by molding or by 3D printing, remain straight at the level of their lateral edges, contrary to the interface dressings of the fourth example (FIG. 11) and the sixth example (FIG. 12), the lateral edges of which are deformed and become concave.

The invention claimed is:

1. An interface dressing consisting of an elastomeric matrix, the elastomeric matrix being provided with a plurality of through-holes, each through-hole having a contour about a central axis,
   wherein at least one part of the plurality of through-holes is arranged so as to form at least one pattern wherein each through-hole is adjacent to at least one other through-hole, the adjacent through-holes having rectangular contours, images of which, when moved translationally in a plane perpendicular to the central axes in order to merge images of said central axes by means of said translational movement, do not become superimposed, wherein, in absence of external strain, the interface dressing has:
a thickness of between 0.4 mm and 2 mm,
a yarn width between two adjacent through-holes of between 0.3 mm and 4 mm,
a grammage of between 200 g/m$^2$ and 1200 g/m$^2$,
wherein, in absence of external strain, each through-hole has a length of between 2 mm and 4 mm and a width of between 1 mm and 2 mm,
wherein lateral edges of the interface dressing remain straight under an applied tensile force test,
wherein the applied tensile force test is conducted by means of a tensile testing machine on a sample of the interface dressing having a width of 10 cm and applying a tensile force in a direction of stretching parallel to a length of the sample at a speed of 100 mm/min with a distance between jaws of 5 cm up to an elongation of 70% of elongation at break, holding the sample at the elongation, and observing the lateral edges,
wherein the elastomeric matrix consists of an elastomeric composition, the adjacent through-holes of the pattern being separated from one another by a yarn of elastomeric composition,
wherein the elastomeric composition comprises a blend of two copolymers, and
wherein the blend comprises at least one copolymer which has a viscosity of between 0.01 and 1 Pas measured in a solution at 5% mass/mass in toluene and at least one copolymer having a viscosity of between 0.01 and 0.5 Pas measured in a solution at 15% (mass/mass) in toluene.

2. The interface dressing as claimed in claim 1, wherein the pattern comprises adjacent through-holes which have identical contours angularly offset from one another about the respective central axes.

3. The interface dressing as claimed in claim 2, wherein the pattern comprises adjacent through-holes which have contours that are each devoid of rotational symmetry about the central axis.

4. The interface dressing as claimed in claim 2, wherein the pattern comprises adjacent through-holes which have contours that each exhibit a rotational symmetry about the central axis with respect to rotation through an angle 2π/n radians, n being an integer, the contours of the adjacent through-holes of the pattern being angularly offset from one another about the respective central axes with angles different than 2π/n radians.

5. The interface dressing as claimed in claim 1, wherein the pattern comprises a network of adjacent through-holes, the central axes of which are aligned in at least a first direction.

6. The interface dressing as claimed in claim 5, wherein the central axes of the adjacent through-holes of the network are aligned in a second direction perpendicular to the first direction.

7. The interface dressing as claimed in claim 1, consisting solely of the elastomeric matrix and devoid of framework supporting the elastomeric composition, so as to be self-supported.

8. The interface dressing as claimed in claim 1, wherein the rectangular contours of the adjacent through-holes are arranged orthogonally relative to one another.

9. The interface dressing as claimed in claim 1, wherein the thickness is between 0.5 mm and 1 mm.

10. The interface dressing as claimed in claim 1, wherein the yarn width is between 0.5 mm and 2 mm.

11. The interface dressing as claimed in claim 1, wherein the yarn width is 0.8 mm.

12. The interface dressing as claimed in claim 1, wherein the grammage is between 300 g/m$^2$ and 800 g/m$^2$.

13. The interface dressing as claimed in claim 1, wherein, in absence of external strain, a total surface area of the plurality of through-holes is 20% to 75% of a total surface area of the interface dressing.

14. The interface dressing as claimed in claim 1, wherein, in absence of external strain, a total surface area of the plurality of through-holes is 30% to 65% of a total surface area of the interface dressing.

15. The interface dressing as claimed in claim 1, wherein the elastomeric matrix extends in a plane and lateral edges of the interface dressing remain straight and in the plane under the applied tensile force test.

16. An interface dressing consisting of an elastomeric matrix, the elastomeric matrix being provided with a plurality of through-holes, each through-hole having a contour about a central axis,
wherein at least one part of the plurality of through-holes is arranged so as to form at least one pattern wherein each through-hole is adjacent to at least one other through-hole, the adjacent through-holes having rectangular contours, images of which, when moved translationally in a plane perpendicular to the central axes in order to merge images of said central axes by means of said translational movement, do not become superimposed,
wherein, in absence of external strain, the interface dressing has:
a thickness of between 0.4 mm and 2 mm,
a yarn width between two adjacent through-holes of between 0.3 mm and 4 mm,
a grammage of between 200 g/m$^2$ and 1200 g/m$^2$,
wherein, in absence of external strain, each through-hole has a length of between 2 mm and 4 mm and a width of between 1 mm and 2 mm,
wherein lateral edges of the interface dressing remain straight under an applied tensile force test,
wherein the applied tensile force test is conducted by means of a tensile testing machine on a sample of the interface dressing having a width of 10 cm and applying a tensile force in a direction of stretching parallel to a length of the sample at a speed of 100 mm/min with a distance between jaws of 5 cm up to an elongation of 70% of elongation at break, holding the sample at the elongation, and observing the lateral edges,
wherein the elastomeric matrix consists of an elastomeric composition, the adjacent through-holes of the pattern being separated from one another by a yarn of elastomeric composition, and
wherein the elastomeric composition comprises, in weight percent relative to a total weight of the elastomeric composition, 5 to 20 wt. % copolymers, 5 to 20 wt. % resins, and 50 to 80 wt. % plasticizer.

17. The interface dressing as claimed in claim 16, consisting solely of the elastomeric matrix and devoid of framework supporting the elastomeric composition, so as to be self-supported.

18. The interface dressing as claimed in claim 16, wherein the pattern comprises adjacent through-holes which have identical contours angularly offset from one another about the respective central axes.

19. The interface dressing as claimed in claim 16, wherein, in absence of external strain, a total surface area of the plurality of through-holes is 20% to 75% of a total surface area of the interface dressing.

20. The interface dressing as claimed in claim 16, wherein, in absence of external strain, a total surface area of the plurality of through-holes is 30% to 65% of a total surface area of the interface dressing.

21. The interface dressing as claimed in claim 16, wherein the pattern comprises adjacent through-holes which have identical contours angularly offset from one another about the respective central axes, and wherein the contours of the adjacent through-holes are each devoid of rotational symmetry about the central axis.

22. The interface dressing as claimed in claim 16, wherein the pattern comprises adjacent through-holes which have identical contours angularly offset from one another about the respective central axes, and wherein the contours or the adjacent through-holes each exhibit a rotational symmetry about the central axis with respect to rotation through an angle $2\pi/n$ radians, n being an integer, the contours of the adjacent through-holes of the pattern being angularly offset from one another about the respective central axes with angles different than $2\pi/n$ radians.

23. The interface dressing as claimed in claim 16, wherein the elastomeric matrix extends in a plane and lateral edges of the interface dressing remain straight and in the plane under the applied tensile force test.

* * * * *